United States Patent [19]

Cardarelli

[11] 4,237,114

[45] * Dec. 2, 1980

[54] METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC DISPENSER

[75] Inventor: Nathan F. Cardarelli, Barberton, Ohio

[73] Assignee: Environmental Chemicals, Inc., Wauconda, Ill.

[ * ] Notice: The portion of the term of this patent subsequent to Aug. 28, 1996, has been disclaimed.

[21] Appl. No.: 5,174

[22] Filed: Jan. 22, 1979

Related U.S. Application Data

[63] Continuation-in-part of Ser. No. 916,570, Jun. 19, 1978, Pat. No. 4,166,111.

[51] Int. Cl.³ ............................................. A01N 55/04
[52] U.S. Cl. ........................................ 424/78; 424/22; 424/83; 424/288
[58] Field of Search ...................... 424/78, 83, 288, 22

[56] References Cited

U.S. PATENT DOCUMENTS

| | | | |
|---|---|---|---|
| 3,417,181 | 12/1968 | Cardarelli | 424/229 |
| 4,010,141 | 3/1977 | Onozuka et al. | 424/78 X |
| 4,012,347 | 3/1977 | Gitlitz et al. | 424/288 X |

OTHER PUBLICATIONS

Chemical Abstracts, 75:97577c, (1971).

*Primary Examiner*—Leonard Schenkman
*Attorney, Agent, or Firm*—Oldham, Oldham, Hudak & Weber Co.

[57] ABSTRACT

A method and composition for destroying pest insects in their aquatic stage and other pest-life forms over a sustained period of time, by the gradual and continuous release of an organotin substance from an inert thermoplastic medium. The composition comprises an organotin of extremely low water solubility bound in an ethylene-vinyl acetate copolymer, or an ethylene-propylene copolymer, in which said organotin is insoluble and in which said organotin is uniformly dispersed with an inert coleachant of moderate or low water solubility. When this formulation is brought into contact with water, the coleachant gradually solvates into the water creating and enhancing the development of porosity within the thermoplastic phase. Said organotin agent, interspersed within the thermoplastic matrix, contacts the entering water and egresses as molecular aggregates being washed through the pore system and into the external watery medium. Such aggregates, being toxic to mosquito larva, other insects and various other pesteferous life forms upon continuous exposure, lead to a condition of terminal chronic intoxication.

70 Claims, No Drawings

METHOD AND COMPOSITION FOR THE LONG TERM CONTROLLED RELEASE OF A NON-PERSISTENT ORGANOTIN PESTICIDE FROM AN INERT MONOLITHIC THERMOPLASTIC DISPENSER

CROSS-REFERENCE

This application is a continuation-in-part of my copending U.S. application bearing U.S. Ser. No. 916,570 filed June 19, 1978 now U.S. Pat. No. 4,166,111 for "A Method and Composition for the Long Term Controlled Release of a Non-Persistent Organotin Pesticide From an Inert Monolithic Thermoplastic Dispenser."

BACKGROUND OF THE INVENTION

This invention relates to certain organotin compounds of the formula $R_3S_nX$ and especially halogenated trialkyl compounds and their dissemination in a continuous and controlled manner into water courses infested with mosquito larva and other susceptible aquatic pest and insect life. Mosquito larva develops through morphogenetic stages in water, emerging in time as adults capable of transmitting dreaded diseases which include encephalitis, malaria, yellow fever, and the like, as well as creating a nuisance to man and man's domestic cattle by their proclivity towards biting and other annoyances. Similarly, other insecta, such as flies of the Simulium family, spend their larval stages in water, emerging as adults capable of transmitting onchocerciasis, a dreaded parasitic disease manifested as blindness in exposed human populaces. Snail hosts of parasitic trematodes, as well as the trematode larva, likewise, dwell in water and can similarly be controlled using the invention described in this specification.

Insects and other bearers of disease are normally and conventionally destroyed through treating the infested waters with larvicidal agents or saturating the air with sprays, fogs, droplets, etc., of specified toxic substances. It is well known that the conventional methodology provides but temporary relief, while of necessity, the use of toxicant concentrations has, as a rule, a significant detrimental ecological effect on non-target organisms, soil, air and water. As described in the monumental text by Cardarelli, 1976, and is now well known to the pesticide formulation and used in the art, through the incorporation of select pesticides in select polymeric matrices, it is possible to cause a slow-long duration release of ultralow concentrations of said pesticides in the pest-infested environment with efficacious benefit and much reduced environmental impact. When target organisms are continuously exposed to very low toxicant concentrations, such concentrations being far too small to materially affect insect control, the gradual accumulation of such agents in the pest body leads to a chronic manifestation of intoxication and eventual mortality.

Slow release toxicant compositions, such as those taught in U.S. Pat. Nos. 3,639,583 and 3,417,181, rely upon release being affected through the now well-known and understood diffusion-dissolution mechanism. It is taught in said patents that release is critically dependent upon the binding polymeric matrix being a solute for the organotin classes used. The binder matrix is a vulcanized or a partially vulcanized elastomer. However, it is well known that generally organotins totally lack solubility in thermoplastic materials and, thus, the diffusion-dissolution process cannot be established.

In other inventions, it has been taught that the pesticidal agents such as organophosphorus class insecticides will similarly release from solute matrices, especially from elastomers. U.S. Pat. No. 3,590,119 is an example of this teaching.

Many mosquito larvicides are known and used in both the conventional sense as well as in controlled release methodologies such as microencapsulation. Among others, Boike et al has shown in examining 23 different organotins in solute elastomer formulations, that they are not effective against the mosquito under practical use situations due to the presence of natural organic substances common to water courses. Said organic materials rapidly absorb organotin molecules essentially removing them from mosquito larva contact.

U.S. Pat. No. 4,012,221 has taught that an elastomer insoluble toxicant, if said toxicant is highly water soluble and is present in relatively high matrix concentrations, can be made to release from said elastomer in excess of 75 parts by weight of toxic per 100 parts of elastomer.

U.S. Pat. No. 3,705,938 teaches that several organophosphorus-type insect adulticides can be incorporated in a laminated polyvinyl chloride structure, wherein no agent solubility exists, and caused to move continuously through said plastic structure to said plastic surface through a volatility mechanism wherein the medium of release is air. Such constructions require the use of a third phase material such as a plasticizer to effect toxicant movement.

U.S. Pat. No. 4,012,347 relates to the antifouling performance of certain asymmetric triorganotin compounds which are incorporated into a coating composition containing a film-forming polymer, a rosin, a solvent, as well as a pigment. Although various film-forming polymers are disclosed including elastomers, the use of an ethylene-vinyl acetate copolymer is not taught. Moreover, the invention leaching rate is very dependent upon the ratio of the rosin to the various polymers.

U.S. Pat. No. 3,234,032 also relates to an anti-fouling marine coating composition wherein various organotin compounds are contained within the film-forming vehicles such as waxes, oils, or a paint having a synthetic polymeric material. Such synthetic materials are the vinyl polymers, the acrylic polymers and the alkyd polymers. Hence, no suggestion of applicant's specific copolymer or coleachant system is taught.

U.S. Pat. No. 3,236,793 relates to a bis(tributyltin)adipate antifouling composition wherein the tin compound is dispersed in a substantially water-insoluble, film-forming vehicle such as spar varnish, vinyl acetate-vinyl chloride copolymer based paints, and the like. Obviously, this patent is unrelated in that it relates to a completely different type of organotin compound, lacks any suggestion of a coleachant system, as well as an ethylene-vinyl acetate copolymer.

Yet another prior art article is that appearing in CHEMICAL ABSTRACTS, 75:97577c (1971) wherein various non-organotin liquid pesticides are dispersed in various film-forming polymers. Once again, this prior art article is readily distinguished from the present invention in that it lacks at least applicant's specific copolymer, organotin compound, as well as the coleachant system.

In pursuance of the invention described herein, it has been discovered that unlike conventional pesticides, specific organotin chemicals act through a hitherto unknown mechanism to effect pest mortality, particularly mosquito and snail mortality. As is well known to the state of the art, organophosphorus, carbamate, halogenated hydrocarbon, and other organic materials affect mortality in insects by interference in vital enzyme systems. It is further well known that this mode of intoxication leads to the unwanted development of resistance to said chemicals through evolutionary processes. In contrast, organotin formulations described herein effect mortality through undiscovered physiological mechanisms that cannot induce tolerance in the target species.

SUMMARY OF THE INVENTION

Accordingly, it is an object of the present invention to provide a method and composition for destroying pests, including insects, usually in their aquatic stage, by utilizing essentially a water-insoluble organotin compound of the formula $R_3Sn_nX$ and especially halogenated trialkyltin compounds having no solubility in a thermoplastic matrix, but dispersed therein and caused to release upon contact with water through the use of a porosity enhancing coleachant of moderate to low water solubility.

It is an additional object of the present invention to provide a method and composition for destroying pests, including insects, as above, wherein said thermoplastic matrix is an ethylene-vinyl acetate copolymer or an ethylene-propylene copolymer which possesses the ability to bind and release organotin compounds.

It is a further object of the present invention to provide a method and composition for destroying pests, including insects, as above, which is not harmful to non-target biota of the environment.

It is another object of the present invention to provide a method and composition for destroying pests, including insects, as above, wherein said organotin compound is slowly released by said thermoplastic compounds and said coleachant.

It is still an additional object of the present invention to provide a method and composition for destroying pests, including insects, as above, wherein said halogenated trialkyltin compound is tributyltin fluoride.

It is still another object of the present invention to provide a method and composition for destroying pests, including insects, as above, wherein said coleachants are inert compounds having a solubility in water of less than 0.1 grams/100 grams of water.

It is still a further object of the present invention to provide a method and composition for destroying pests, including insects, as above, wherein a high mortality rate of said pest insects is produced.

It is yet another object of the present invention to provide a method and composition for destroying pests, including insects, as above, wherein said organotin compound is slowly released for an extended period of time, as from several weeks to a plurality of years.

These and other objects of the present invention will become apparent from the following specification describing in detail the preferred embodiment of the invention.

In general, a composition for destroying pests over a period of years, comprises: 100 parts by weight of a polymer matrix selected from the class consisting of an ethylene-vinyl acetate copolymer, an ethylene-propylene copolymer, and combinations thereof, the amount by weight of said ethylene constituent in said ethylene-vinyl acetate copolymer ranging from about 60 percent to about 95 percent, said ethylene-vinyl acetate copolymer having a molecular weight of from about 40,000 to about 400,000, the amount by weight of said ethylene constituent and said ethylene-propylene copolymer ranging from about 30 percent to about 80 percent, the weight average molecular weight of said ethylene-propylene copolymer ranging from about 50,000 to about 250,000;

from about 25 to about 75 parts by weight per 100 parts of said copolymer matrix of a toxicant, said toxicant having the formula $R_3Sn_nX$, wherein R is selected from the class consisting of an alkyl group having from 1 to 8 carbon atoms, an aryl group, and a substituted aryl group, wherein said substituted group is an alkyl or an ester containing from 1 to 6 carbon atoms; X is selected from the class consisting of a halogen, an oxide, an alkoxy $OR^1$ where $R^1$ is an alkyl having from 1 to 12 carbon atoms, or an

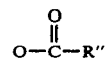

group where R″ is an alkyl having from 1 to 12 carbon atoms; and from about 15 to about 70 parts by weight per 100 parts of said polymer matrix of an inert coleachant compound, said coleachant compound having a solubility in water of 0.1 grams or less per 100 grams of water.

Additionally, a process for destroying pests by the gradual and continual release of an organotin toxicant from a thermoplastic matrix, comprises the steps of: preparing a mixture of the organotin toxicant, a polymer matrix, and a coleachant; the amount of said polymer matrix being 100 parts by weight and selected from the class consisting of an ethylene-vinyl acetate copolymer, an ethylene-propylene copolymer, and combinations thereof, said ethylene-vinyl acetate copolymer having a molecular weight of from about 40,000 to about 400,000 and containing from about 60 to about 95 percent by weight of ethylene, said ethylene-propylene copolymer having a molecular weight of from about 50,000 to about 250,000, and having from about 30 percent to about 80 percent ethylene by weight; the amount of said organotin toxicant ranging from about 25 parts to about 75 parts by weight per 100 parts of said polymer matrix, said organotin toxicant having the formula $R_3Sn_nX$ wherein R is selected from the class consisting of an alkyl group having from 1 to 8 carbon atoms, an aryl group, and a substituted aryl group, wherein said substituted group is an alkyl or an ester containing from 1 to 6 carbon atoms; X is selected from the class consisting of a halogen, an oxide, an alkoxy $OR^1$ where $R^1$ is an alkyl having from 1 to 12 carbon atoms, or an

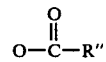

group where R″ is an alkyl having from 1 to 12 carbon atoms; from about 15 to about 70 parts by weight per 100 parts of said polymer matrix of an inert coleachant having a solubility in water of 0.1 grams or less per 100 grams of water; and, applying said mixture to an environment so that upon contact with water, said organotin compound egresses from said polymer matrix.

DESCRIPTION OF THE PREFERRED EMBODIMENT

The present invention relates to the sustained release of an organotin composition which is very effective against pests, particularly mosquito larva and can also be utilized against molluscan hosts of trematode parasites and, in some cases, the aquatic larval forms of such parasites, as well as other aquatic pests. The compositions involved permit a long duration controlled release of the said organotin in ultralow aggregate concentrations in water that result in the gradual accumulation of said agents within the responsive target pest tissues, chronic intoxication and eventual mortality. However, it is believed from empirical evidence that the organotins absorbed by or ingested by target species are both proteolytic and antimorphogenetic; and, because of the nature of such mechanisms leading to mortality for the target to acquire resistance would necessitate evolving new proteins and peptide linkages.

The pesticide composition consists of an organotin possessing either low or very low water solubility and no thermoplastic solubility, bound and uniformly dispersed in a thermoplastic ethylene vinyl-acetate copolymer or an ethylenepropylene copolymer, wherein also uniformly dispersed is an inert material of moderate or low water solubility that serves a porosigenic function. The porosigen is a coleachant; but, unlike the elastomer-high toxicant system taught in U.S. Pat. No. 4,012,221, functions only to induce and enhance porosity within the matrix and has no function as an interfacial pH regulant. In the present invention, the organotin toxicant is generally monolithically dispersant in association with the porosity enhancing coleachant.

The specific organotin compounds of the present invention have the formula $R_3S_nX$ wherein R, the organo group, is an alkyl group having from 1 to 8 carbon atoms, desirably from 3 to 6 carbon atoms, with preferably 3 carbon atoms, that is propyl and the isomers thereof being highly preferred. An alkyl group containing 4 carbon atoms, that is butyl and the various isomers thereof is highly preferred. Additionally, the organo portion R of the tin toxicant may be an aryl group or a substituted aryl group with the substituted portion being an alkyl or an ester group containing from 1 to 6 carbon atoms. Specific examples of such compounds include phenyl, phenyl acetate, phenyl propionate, phenyl isobutyrate, and the like.

The anion or "X" portion of the organotin compound can be a halogen, an oxide, an alkoxy $OR^1$ wherein $R^1$ is an alkyl and contains from 1 to 12 carbon atoms, or an

group where R" is an alkyl having from 1 to 12 carbon atoms such as propionate, butyrate, pentyate, hexylate, and the like, with acetate being preferred. Of the various anions, the halogens are preferred, with fluorine being highly preferred.

Thus, a highly preferred alkyl compound of the present invention is tributyltin fluoride. Desired aryl compounds are triphenyltin fluoride and triphenyltin acetate.

The solubility of the organotin compounds in a thermoplastic matrix or binder is nil, as noted, and very low in water; that is, approximately 3 parts per million by weight or less. The amount of organotin compound utilized by weight per 100 parts of polymer matrix binding agent ranges from about 25 parts to about 75 parts, with from about 40 parts to 70 parts being preferred. Naturally, smaller or higher amounts may be utilized, but these aforesaid ranges result in very effective pest-toxicant thermoplastic matrixes.

The polymer matrix or binding agent of the present invention relates to ethylene-vinyl acetate copolymers since they have been found to possess the ability to bind and release halogenated organotin compounds. Such copolymers are readily available in commerce and the amount by weight of the ethylene repeating units, based upon the total weight of the copolymer, ranges from about 60 percent to about 95 percent with a range of from about 80 percent to about 93 percent being preferred. The weight average molecular weight of the copolymer generally ranges from about 40,000 to about 400,000 and preferably from about 75,000 to about 300,000. Desirably, the copolymer has an ASTM Test #D-1238 melt flow index of from about 6 to about 12 and preferably from about 7 to about 11 and a Vicat softening point of from about 70° C. to about 95° C. Since, apparently, the ethylene repeating units in the copolymer act as a regulator with regard to pore size, higher amounts of the ethylene constituent will result in slower release times.

Additionally, the polymer matrix or binding agent can also be an ethylene-propylene copolymer having a weight average molecular weight of from about 50,000 to about 250,000 with a preferred range of from about 100,000 to about 200,000. The percent by weight of the ethylene portion can generally vary from about 30 percent to about 80 percent and preferably from about 45 percent to about 75 percent. The melt flow index of the ethylene-propylene copolymer can generally range from about 15 to about 45 and preferably from about 20 to about 32 according to ASTM Test #D-1238 at 190° C., 21,600 gms, gm/10 minutes.

Although the ethylene-propylene copolymer gives good results, the ethylene-vinyl acetate copolymer, with or without the low density polyethylene, is preferred.

Moreover, in order to promote long release duration, it has been found useful, although not necessary, to blend the ethylene-vinyl acetate copolymer or the ethylene-propylene copolymer, or combinations thereof, with a polyethylene, especially low density polyethylene (that is, a density of from about 0.90 to 0.94 g/cc), having a melt flow index similar to said ethylene-vinyl acetate copolymer, that is from about 5 to about 14 and, preferably from about 7 to about 11, and a weight average molecular weight of from about 100,000 to about 400,000. Thus, depending upon the rate of release, various amounts of low density polyethylene may be utilized. Generally, to obtain desirable release rates, the amount of homopolyethylene utilized may range from about 30 percent to about 75 percent and, preferably, from about 40 percent to about 60 percent by weight, based upon the total weight of the blend of the ethylene-vinyl acetate copolymer, or the ethylene-propylene copolymer, or combinations thereof, and the polyethylene.

A number of moderate or low solubility compounds can be utilized as a coleachant or porosity-inducing agent. By moderate or low solubility, it is meant that the solubility is approximately 0.1 or less and preferably 0.01 grams or less, per 100 grams of water. Generally, any compound which is inert with respect to the polymer matrix and the organotin toxicant can be utilized. By inert, it is meant that the coleachant does not chemically react with the polymer matrix or the toxicant. Desirably, the coleachant is also not damaging or harmful to the environment such as the various mercury, cadmium, arsenic compounds, and the like. Thus, the coleachant can be any compound which meets these requirements and is set forth in the Handbook of Chemistry and Physics, published by The Chemical Rubber Co., 1977-78 Edition, and is hereby fully incorporated by reference. A suitable class of an inert coleachant compound includes salts or oxides. The cation of such a salt may generally be any of the alkaline metals, and preferably any of the alkaline earth metals, Column 1A and 2A, respectively of the Periodic Table. Additionally, various other metals may be utilized such as iron, nickel, zinc, tin, silver and the like. The anion portion of the salt may generally be any negative charge entity charge as the various carbonates, the various nitrates, nitrites, or nitrides, the various sulfates, sulfites, or sulfides, the various phosphates, phosphites, or phosphides, including the ortho, pyro, hypo, variations thereof, and the like. Generally, the sulfates, sulfites and sulfides are preferred as anions, with carbonates being highly preferred. Moreover, as noted above, the anion may be an oxide of the metal. Specific examples of coleachants include magnesium carbonate, magnesium sulfide, magnesium phosphide, magnesium oxide, calcium carbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfite, lithium phosphate, beryllium oxide, strontium carbonate, strontium sulfate, and strontium sulfite. Magnesium, strontium and barium carbonates are preferred with calcium carbonate being highly preferred. The amount of coleachant generally varies from about 15 parts to about 70 parts by weight based upon 100 parts of said polymer matrix (that is, said copolymer or said blend of said polyethylene and said copolymer), and preferably from about 25 to about 60 parts.

The composition can contain, in addition to the above-mentioned components, various well known and conventional additives to enhance dispersion, add color, aid in processing, or to alter the density. For example, should a composition be desired to sink, any composition having a specific gravity greater than 1 may be added in the necessary amounts to render the overall specific gravity of the material to be greater than 1. Naturally, a non-reactive, relatively inert and non-polluting or detrimental compound to the environment is desired such as silicon dioxide, iron oxide, various coarse clays, and the like. Carbon black may be utilized as a regulator. An example of the dispersant to aid in establishing a uniformed distribution of the organotins such as the tributyltin fluoride compound is zinc stearate in suitable amounts, as from 0.2 parts to about 10 or 20 parts by weight, per 100 parts by weight of the polymer. Furthermore, the composition can contain suitable amounts of an attractant-porosigen such as from about 12 to about 25 parts of soy oil or lecithin, when not utilized in an aqueous or liquid environment.

In order to form a suitable thermoplastic dispenser which releases suitable amounts of an organotin pesticide through a coleachant system, it is desirable that the particle sizes of the various components be relatively small. For example, it is desirable that the organotin compounds have a Tyler mesh size of roughly 100 or greater (i.e., a particle size smaller than 100 mesh) and preferably smaller than 200 mesh. Accordingly, a particle size range for the coleachant is generally the same. The particle size of the ethylene-vinyl acetate copolymer or the blend of polyethylene and the ethylene-vinyl acetate copolymer is roughly about 50 to 200 Tyler mesh. Since the composition is made by heating and melting the polymer, the polymer size is not very important.

The pesticide is prepared by mixing the halogenated organotin compound with the polymer matrix and the coleachant in suitable proportions as indicated above in any conventional mixing apparatus along with various additives such as colorants, dispersants, and the like. The mixture is then coalesced by heating at least above the softening point and preferably above the melting point of the polymer and is partitioned for use in any suitable size or shape, for example, pellet, chip, ribbon or ribbon form. For example, the mixture may be added to a conventional extruder where it is molded at about 170° C. to about 190° C. in a suitable form such as a rod, which may be cut up into appropriate pellet sizes. The invention will be better understood by reference to the following examples.

EXAMPLES

The components listed in Table I below were blended by roll mixing, adding the blender to the hopper of a conventional plastic extruder which was then extruded as a rod or a sheet of set dimensions. Since the release rate is proportional to the surface area, the surface to volumn ratio is a major determinant of lifetime. Consequently, the extruded rod or sheet is commuted to a predetermined dimension commensurate with the desired biocidal lifetime.

TABLE I

|  | EXAMPLE 1 | EXAMPLE 2 | EXAMPLE 3 | EXAMPLE 4 |
|---|---|---|---|---|
|  |  | Parts by Weight |  |  |
| Ethylene-vinyl acetate copolymer | 56.2 | 28.6 | 22.0 | 43.0 |
| Polyethylene | — | 27.6 | 22.0 | — |
| Zinc stearate | 2.4 | 2.4 | 1.0 | 2.0 |
| Calcium carbonate | 17.0 | 17.0 | 25.0 | 17.0 |
| Silicon dioxide | — | — | — | 8.0 |
| Tributyltin fluoride | 24.4 | 24.4 | 30.0 | 30.0 |

The ethylene-vinyl acetate copolymer used in Table I was Microthene MU 763 (9 percent vinyl acetate) having a melt flow index of 9.0. Zinc stearate, silicon dioxide and calcium carbonate were finely divided particles of 200 or greater mesh size for adequate dispersion. The low density polyethylene material was Microthene MN 718, having a density of 0.917 g/cc and a melt flow index of 8.5. (Microthene is the trademark of U.S.I. Chemicals of New York, N.Y.)

Example 1 above is a fast-release floating material useful in vegetatively overgrown stagnant water, or as an anchored ribbon in catch basins or similar mosquito breeding sites wherein periodic flushing with water would normally wash away a pellet or granule. Example 2 is a slow release material which floats due to its low density. Example 3 is a slow-release sinking material and Example 4 is a fast release sinking composition. It has also been observed that release is not molecular, as seen with elastomer binding matrices, but rather the organotin leachant is an aggregate of molecules whose cohesiveness or attraction to each other is dramatically greater than their attraction to suspended or dissolved natural organic constituents of water so that combination and effective detoxification proceeds at a relatively slow rate.

Materials such as those shown in Table 1 have been examined in periodic challenge bioassay and the $LT_{100}$ (lethal time to 100 percent population mortality) determined, using the larval Culicine mosquito species as the test animal. Table II is a compendium of values for Formulation No. 3 (Example 3).

TABLE II

FORMULATION NO. 3-vs-*Culex Pipiens* Quinquefasciatus LARVA
(First and Second Instar)[1]

| Total Available Agent[2] (ppm) | Immersion Time (days) | $LT_{100}$ (days) | Immersion Time (days) | $LT_{100}$ (days) | Immersion Time (days) | $LT_{100}$ (days) |
|---|---|---|---|---|---|---|
| 12.5 | 30 | 2 | 106 | 4 | 160 | 4 |
| 8.0 | 30 | 3 | 106 | 9 | 160 | 8 |
| 4.1 | 30 | 7 | 110 | 13 | 160 | 12 |
| 2.7 | 30 | 8 | 106 | 13 | 160 | — |
| 2.3 | 30 | 10 | 110 | 4 | 160 | 8 |
| 1.4 | 30 | 10 | 110 | 13 | 160 | 11 |
| 0.47 | 30 | 8 | 110 | 13 | 160 | 12 |
| 12.5 | 225 | 5 | 310 | 12 | | |
| 8.0 | 225 | 7 | 310 | 13 | | |
| 4.1 | 225 | 9 | 310 | 13 | | |
| 2.7 | 225 | 10 | 310 | 15 | | |
| 2.3 | 225 | 12 | 310 | * | | |
| 1.4 | 225 | 12 | 310 | * | | |
| 0.47 | 225 | 10 | 310 | * | | |

[1]Seventy-five mosquito larvae in five separate containers were bioassayed at each concentration. Pellets are continuously immersed with periodic water change between tests.
[2]Total available agent refers to the amount within the pellets, prior to immersion, and not to the water concentration.

The threshold tributyltin fluoride release rate is approximately 0.0097 parts-per-million per day.

Long term results, from another bioassay series, are shown in Table III.

TABLE III

FORMULATION NOS. 2 and 3 -vs- CULCINE LARVA
(First and Second Instars)

| Formulation | Total Available Agent (ppm) | Immersion Time (days) | Larva $LT_{100}$ (days) | Percent Pupation | Percent Adult |
|---|---|---|---|---|---|
| No. 2 | 30.2 | 481 | 7 | 0 | 0 |
| | 16.3 | 481 | 5 | 0 | 0 |
| | 6.9 | 470 | 10 | 7 | 0 |
| | 4.3 | 470 | 16 | 20 | 0 |
| | 1.95 | 495 | 16 | 20 | 0 |
| No. 3 | 32.6 | 407 | 5 | 0 | 0 |
| | 16.3 | 473 | 5 | 0 | 0 |
| | 5.94 | 483 | 11 | 0 | 0 |
| | 5.61 | 512 | 10 | 0 | 0 |
| | 5.22 | 485 | 8 | 0 | 0 |
| | 5.19 | 497 | 15 | 13 | 0 |
| | 4.80 | 492 | 14 | 0 | 0 |
| | 2.46 | 473 | 15 | 40 | 0 |
| | 1.92 | 485 | 15 | 13 | 7 |
| | 0.92 | 485 | 16 | 13 | 13 |

Several salient features were observed that contributed to the uniqueness of this system. Unlike almost all conventionally used mosquito larvicides, these substances are effective pupacides. Also, morphogenetic damage was dramatically evident. In the normal sequence of events, morphogenesis from instar to instar occurs at one, two, or three-day intervals for the four larval instars characteristic of the test species. In general, such changes did not occur. For instance, second instar larva remained at that stage of development for up to 13 days, whereas normal metamorphosis to the third instar would occur in two or three days.

In bioassay measurements against molluscs in general and *Biomphalaria glabrata* snails in particular, effective biocidal action is noted using the subject invention. It is well known to the state-of-the-art that various organotin agents, including tributyltin fluoride can be released from elastomeric material with efficacious molluscicidal activity seen. Heretofore, it has not been possible to utilize plastic materials in this usage and indeed the state-of-the-art has believed that effective release of organotins from nonsolute polymers such as plastics could not be achieved.

Long term results using the formulations given above have been observed in bioassay against said snails as shown in Table IV. It is noted that *Biophalaria glabrata* is a major host snail for the *Schistosoma mansoni* parasite, the causative agent for the dreaded major human disease, "Schistosomiasis."

TABLE IV

FORMULATIONS 2 and 3 -vs- ADULT BIOPHALARIA GLABRATA SNAILS
(5 replicates × 10 snails/replicate)

| Formulation | Total Available Agent (ppm) | Immersion Time (days) | $LT_{100}$ (days) | Immersion Time | $LT_{100}$ (days) | Immersion Time | $LT_{100}$ (days) |
|---|---|---|---|---|---|---|---|
| No. 2 | 10 | 0 | 4 | 60 | 10 | 120 | 12 |
| | 5.4 | 0 | 6 | 60 | 11 | 120 | 21 |
| | 2.3 | 0 | 7 | 60 | 19 | 120 | 40 |
| | 1.4 | 0 | 8 | 60 | 24 | 120 | — |
| | 0.6 | 0 | 12 | 60 | 28 | 120 | — |
| | 10 | 240 | 15 | — | — | — | — |
| NO. 3 | 12.5 | 0 | 4 | 60 | 7 | 120 | 9 |
| | 8.2 | 0 | 6 | 60 | 8 | 120 | 10 |
| | 2.0 | 0 | 8 | 60 | 9 | 120 | 17 |
| | 1.9 | 0 | 8 | 60 | 11 | 120 | 21 |
| | 1.7 | 0 | 9 | 60 | 15 | 120 | 22 |
| | 1.7 | 0 | 9 | 60 | 15 | 120 | 24 |
| | 1.6 | 0 | 9 | 60 | 17 | 120 | 26 |

TABLE IV-continued

FORMULATIONS 2 and 3 -vs- ADULT BIOPHALARIA GLABRATA SNAILS (5 replicates × 10 snails/replicate)

| Formulation | Total Available Agent (ppm) | Immersion Time (days) | $LT_{100}$ (days) | Immersion Time | $LT_{100}$ (days) | Immersion Time | $LT_{100}$ (days) |
|---|---|---|---|---|---|---|---|
| | 0.8 | 0 | 12 | 60 | 19 | 120 | 30 |
| | 0.6 | 0 | 14 | 60 | 22 | 120 | 35 |
| | 12.5 | 240 | 8 | | | | |
| | 8.2 | 240 | 11 | | | | |
| | 4.1 | 240 | 14 | | | | |
| | 2.3 | 240 | 22 | | | | |

In bioassy tests against both larva forms of the Schistosoma mansoni schistosome, it is observed that extremely low toxicant levels are effective (Table V).

TABLE V

FORMULATIONS 2 and 3 -vs- SCHISTOLARVA

| Formulation | Total Available Toxicant | $LT_{100}$ (min.) Miracidia | Cercariae |
|---|---|---|---|
| No. 2 | 0.008 ppm | 60 | 60 |
| | 0.0008 ppm | 180 | 120 |
| | 0.00008 ppm | 240 | 480 |
| No. 3 | 0.008 ppm | 60 | 60 |
| | 0.0008 ppm | 60 | 120 |
| | 0.00008 ppm | 240 | 480 |

Although the $LT_{100}$ is considered the indicium of effectiveness, it is noted that larvae mobility ceases in a shorter duration and the cercarial form loses the ability to infect a susceptible host in still less time. It is, thus, postulated that unlike conventional materials of a molluscicidal or cercariacidal nature, long lasting formulations, as reported herein, can be effectively used in ultra low concentrations as a means of intervening the Schistosomiasis transmission cycle, thus, offering substantial protection to humans contacting the infested waters.

The use of toxic materials against target pests often results in ecological damage through concomitant effects upon nontarget biota. Environmental impact and toxicity tests using the four formulations of Table I indicate a relatively low effect on various life forms associated with the aquatic habitat. Floating aquatic plants such as *Lemna* (duckweed) and *Eichornia crassipes* (water hyacinth) are unaffected in thirty-day bioassay evaluations. In contrast, *Elodea canadensis,* when rooted, is susceptible to intoxication at 10 ppm and 1 ppm dosages. Microorganisms such as monocellular green algae and other phytoplankters show relatively little population suppression and the effects seen are reversible after thirty to sixty days post exposure. Field reports have confirmed laboratory studies. Fish are unaffected at 10 ppm total active concentrations as shown in standard bioassay using *Lebistes reticulatus* as a moderately susceptible fish species. In mouse toxicity and teratogenicity studies, no gross physciological or behavior effects are noted over four generations, whose water supply was treated with Formulation 3 at 10 ppm. Rats fed Formulation 3, using standard toxicity tests, indicate a mammalian $LD_{50}$ in excess of 2,000 mg/kg.

While in accordance with the patent statutes, the best mode and preferred embodiment has been described in detail, the invention is to be measured by the appended claims.

What is claimed is:

1. A composition for destroying aquatic pests over a period of time, comprising:

100 parts by weight of a polymer matrix selected from the group consisting of an ethylene-vinyl acetate copolymer, and ethylene-propylene copolymer, and combinations thereof, the amount by weight of said ethylene constituent in said ethylene-vinyl acetate copolymer ranging from about 60 percent to about 95 percent, said ethylene-vinyl acetate copolymer having a molecular weight of from about 40,000 to about 400,000, the amount by weight of said ethylene constituent and said ethylene-propylene copolymer ranging from about 30 percent to about 80 percent, the weight average molecular weight of said ethylene-propylene copolymer ranging from about 50,000 to about 250,000;

from about 25 to about 75 parts by weight per 100 parts of said copolymer matrix of a toxicant, said toxicant having the formula $R_3S_nX$, where R is selected from the group consisting of an alkyl group having from 1 to 8 carbon atoms, or an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms, or an group where R″ is an alkyl having from 1 to 12 carbon atoms; and from about 15 to about 70 parts by weight per 100 parts of said polymer matrix of a moderate to low solubility porosity inducing agent, said porosity inducing agent selected from the group consisting of a non-alkaline earth salt, and a non-alkaline earth oxide, said porosity inducing agent having a solubility in water of 0.1 grams or less per 100 grams of water.

2. A composition according to claim 1, wherein X of said toxicant is selected from the group consisting of halogen, oxygen, and an acetate group, wherein said alkyl group contains from 3 to 6 carbon atoms, and wherein said aryl group is phenyl.

3. A composition according to claim 2, wherein the amount of ethylene by weight in said ethylene-vinyl acetate copolymer ranges from about 80 percent to about 93 percent, wherein the amount of ethylene in said ethylene-propylene copolymer ranges from about 45 to about 75 percent by weight, wherein the amount of said toxicant ranges from about 40 to about 70 parts by weight, wherein said alkyl group of said toxicant contains 3 to 4 carbon atoms, and wherein the amount of said porosity inducing agent ranges from about 25 to about 60 parts by weight and has a solubility of 0.01 grams or less per 100 grams of water.

4. A composition according to claim 3, wherein said copolymer is said ethylene-vinyl acetate copolymer.

5. A composition according to claim 1, wherein said porosity inducing agent; compound is selected from the group consisting of an oxide and a salt, said oxide and salt having a cation selected from the group consisting of the alkaline metals, iron, zinc, nickel, silver, and tin, and said salt having an anion selected from the group consisting of a carbonate, bicarbonate, nitrate, nitrite, nitride, peroxide, phosphate, phosphite, phosphide, sulfate, sulfite and sulfide.

6. A composition according to claim 5, wherein said copolymer is said ethylene-vinyl acetate copolymer.

7. A composition according to claim 5, wherein said X of said toxicant is selected from the group consisting of halogen, oxygen, or acetate, wherein said alkyl group contains from 3 to 6 carbon atoms, and where said aryl group is phenyl.

8. A composition according to claim 7, wherein said porosity inducing agent is selected from the group consisting of iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfite, lithium phosphate.

9. A composition according to claim 6, wherein said copolymer is said ethylene-vinyl acetate copolymer.

10. A composition according to claim 8, wherein said toxicant is selected from the group consisting of tributyltin fluoride, tributyltin oxide, triphenyltin fluoride, triphenyltin acetate, and combinations thereof.

11. A composition according to claim 10, wherein the amount of ethylene by weight in said ethylene-vinyl acetate copolymer ranges from about 80 percent to about 93 percent, wherein the amount of ethylene in said ethylene-propylene copolymer ranges from about 45 to about 75 percent by weight, wherein the amount of said toxicant ranges from about 40 to about 70 parts by weight, and wherein the amount of said porosity inducing agent ranges from about 25 to about 60 parts by weight and has a solubility of 0.01 grams or less per 100 grams of water.

12. A composition according to claim 11, wherein said copolymer is said ethylene-vinyl acetate copolymer.

13. A composition according to claims 1, 2 or 3, and further including with said ethylene-vinyl acetate copolymer or said ethylene-propylene copolymer from about 30 percent to about 75 percent by weight of a low density polyethylene based upon the total weight of said polyethylene and said copolymer, said polyethylene having a density of from about 0.90 to about 0.940 g/cc and a weight average molecular weight of from about 100,000 to about 400,000.

14. A composition according to claim 13, wherein said toxicant is selected from the group consisting of tributyltin fluoride, tributyltin oxide, triphenyltin fluoride, and triphenyltin acetate, wherein said ethylene-vinyl acetate has a melt flow index of from about 6 to about 12, wherein said low density polyethylene has a melt flow index of from about 5 to about 14, and wherein said ethylene-propylene copolymer has a melt flow index of from about 15 to about 45.

15. A composition according to claim 7 or 11, and further including with said ethylene-vinyl acetate copolymer or said ethylene-propylene copolymer from about 30 percent to about 75 percent by weight of a low density polyethylene based upon the total weight of said polyethylene and said copolymer, said polyethylene having a density of from about 0.90 to about 0.940 g/cc and a weight average molecular weight of from about 100,000 to about 400,000.

16. A composition according to claim 15, wherein said ethylene-vinyl acetate has a melt flow index of from about 6 to about 12, wherein said low density polyethylene has a melt flow index of from about 5 to about 14, and wherein said ethylene-propylene copolymer has a melt flow index of from about 15 to about 45.

17. A composition according to claim 16, wherein said porosity inducing agent is selected from the group consisting of iron carbonate, nickel carbonate, zinc carbonate.

18. A composition according to claim 17, wherein said copolymer is said ethylene-vinyl acetate copolymer.

19. A composition for destroying aquatic pests over a period of time, comprising:
100 parts by weight of an ethylene-propylene copolymer, the amount by weight of said ethylene constituent in said ethylene-propylene copolymer ranging from about 30 percent to about 80 percent, the weight average molecular weight of said ethylene-propylene copolymer ranging from about 50,000 to about 250,000;
from about 25 to about 75 parts by weight per 100 parts of said copolymer matrix of a toxicant, said toxicant having the formula $R_3Sn_nX$, wherein R is selected from the group consisting of an alkyl group having from 1 to 8 carbon atoms, or an aryl group, and a substituted aryl group wherein said substituted group is an alkyl or an ester containing from 1 to 6 carbon atoms; X is selected from the group consisting of a halogen, an oxide, an alkoxy $OR^1$ where $R^1$ is an alkyl having from 1 to 12 carbon atoms, or an

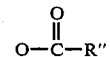

group where R″ is an alkyl having from 1 to 12 carbon atoms; and
from about 15 to about 70 parts by weight per 100 parts of said polymer matrix of a moderate to low soluble porosity inducing agent, said porosity inducing agent selected from the group consisting of an alkaline earth salt and an alkaline earth oxide having a solubility in water of 0.1 grams or less per 100 grams of water.

20. A composition according to claim 19, wherein said porosity inducing agent is selected from the group consisting of an oxide and a salt, said salt having an anion selected from the class consisting of carbonate, bicarbonate, nitrate, nitrite, nitride, peroxide, phosphate, phosphite, phoside, sulfate, sulfite, and sulfide.

21. A composition according to claim 20, wherein said X of said toxicant is selected from the group consisting of halogen, oxygen, or acetate, said alkyl group contains from 3 to 6 carbon atoms, and said aryl group is phenyl.

22. A composition according to claim 21, wherein said porosity inducing agent is selected from the group consisting of magnesium carbonate, magnesium sulfide, magnesium phosphides, magnesium oxide, calcium carbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, beryllium oxide, strontium carbonate, strontium sulfate, and strontium sulfite.

23. A composition according to claim 22, wherein said toxicant is selected from the group consisting of tributyltin fluoride, tributyltin oxide, triphenyltin fluoride, triphenyltin acetate, and combinations thereof.

24. A composition according to claim 23, wherein the amount of ethylene in said ethylene-propylene copolymer ranges from about 45 to about 75 percent by weight, wherein the amount of said toxicant ranges from about 40 to about 70 parts by weight, and wherein the amount of said porosity inducing agent ranges from about 25 to about 60 parts by weight and has a solubility of 0.01 grams or less per 100 grams of water.

25. A composition according to claims 19, or 20 or 24, including from about 30 percent to about 75 percent by weight of a low density polyethylene based upon the total weight of said low density polyethylene and said ethylene-propylene copolymer, said polyethylene having a density of from about 0.90 to about 0.940 g/cc and a weight average molecular weight of from about 100,000 to about 400,000.

26. A composition according to claim 25 wherein said low density polyethylene has a melt flow index of from about 5 to about 14 and wherein said ethylene-propylene copolymer has a melt flow index of from about 15 to about 45.

27. A composition according to claim 26, wherein said porosity inducing agent is selected from the group consisting of magnesium carbonate, calcium carbonate, barium carbonate, and strontium carbonate.

28. A composition according to claim 27, wherein said porosity inducing agent is calcium carbonate.

29. A composition for destroying aquatic pests over a period of time, comprising:
100 parts by weight of a polymer matrix selected from the group consisting of an ethylene-vinyl acetate copolymer, an ethylene-propylene copolymer, and combinations thereof, the amount by weight of said ethylene constituent in said ethylene-vinyl acetate copolymer ranging from about 60 percent to about 95 percent, said ethylene-vinyl acetate copolymer having a molecular weight of from about 40,000 to about 400,000, the amount by weight of said ethylene constituent and said ethylene-propylene copolymer ranging from about 30 percent to about 80 percent, the weight average molecular weight of said ethylene-propylene copolymer ranging from about 50,000 to about 250,000;
from about 25 to about 75 parts by weight per 100 parts of said copolymer matrix of a toxicant, said toxicant having the formula $R_3Sn_nX$, where R is selected from the group consisting of an alkyl group having from 1 to 8 carbon atoms, or an aryl group, and a substituted aryl group wherein said substituted group is an alkyl or an ester containing from 1 to 6 carbon atoms; X is selected from the group consisting of an oxide or an alkoxy $OR^1$ where $R^1$ is an alkyl having from about 1 to 12 carbon atoms, or an

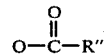

group where R'' is an alkyl having from 1 to 12 carbon atoms; and
from about 15 to about 70 parts by weight per 100 parts of said polymer matrix of a moderate to low solubility porosity inducing agent, said porosity inducing agent selected from the group consisting of an alkaline earth salt or an alkaline earth oxide, said porosity inducing agent having a solubility in water of 0.1 grams or less per 100 grams of water.

30. A composition according to claim 29, wherein said porosity inducing agent is selected from the group consisting of an oxide or a salt, said salt having an anion selected from the group consisting of carbonate, bicarbonate, nitrate, nitrite, nitride, peroxide, phosphate, phosphite, phosphide, sulfate, sulfite, and sulfide.

31. A composition according to claim 30, wherein said X of said toxicant is selected from the group consisting of oxygen or acetate, said alkyl group contains from 3 to 6 carbon atoms, and said aryl group is phenyl.

32. A composition according to claim 31, wherein said porosity inducing agent is selected from the group consisting of magnesium carbonate, magnesium sulfide, magnesium phosphides, magnesium oxide, calcium carbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, beryllium oxide, strontium carbonate, strontium sulfate, and strontium sulfite.

33. A composition according to claim 32, wherein the amount of ethylene by weight in said ethylene-vinyl acetate copolymer ranges from about 80 percent to about 93 percent, wherein the amount of ethylene in said ethylene-propylene copolymer ranges from about 45 percent to about 75 percent by weight, wherein the amount of said toxicant ranges from about 40 to about 70 parts by weight, and wherein the amount of said porosity inducing agent ranges from about 25 to about 60 parts by weight.

34. A composition according to claim 33, wherein said toxicant is selected from the group consisting of tributyltin oxide, triphenyltin acetate, and combinations thereof.

35. A composition according to claim 29, 30, 31, 32, 33, or 34, including from about 30 percent to about 75 percent by weight of a low density polyethylene based upon the total weight of said low density polyethylene and said ethylene-vinyl acetate copolymer or said ethylene-propylene copolymer, said polyethylene having a density of from about 0.90 to about 0.94 grams per cc and a weight average molecular weight of from about 100,000 to about 400,000.

36. A composition according to claim 35, wherein said ethylene-vinyl acetate has a melt flow index of from about 6 to about 12, wherein said low density polyethylene has a melt flow index of from about 5 to about 14, and wherein said ethylene-propylene copolymer has a melt flow index of from about 15 to about 45.

37. A composition according to claim 36, wherein said porosity inducing agent is selected from the group consisting of magnesium carbonate, calcium carbonate, barium carbonate, and strontium carbonate.

38. A composition according to claim 37, wherein said porosity inducing agent is calcium carbonate.

39. A process for destroying aquatic pests by the gradual and continual release of an organotin toxicant from a thermoplastic matrix, comprising applying said aquatic pest composition of claim 1 to an aquatic environment.

40. A process according to claim 39, wherein X of said toxicant is selected from the group consisting of halogen, oxygen, and acetate, wherein said alkyl group contains from 3 to 6 carbon atoms, and wherein said aryl group is phenyl.

41. A process according to claim 40, wherein the amount of ethylene by weight in said ethylene-vinyl acetate copolymer ranges from about 80 percent to about 93 percent, wherein the amount of ethylene in said ethylene-propylene copolymer ranges from about 45 to about 75 percent by weight, wherein the amount of said toxicant ranges from about 40 to about 70 parts by weight, wherein said alkyl group of said toxicant contains 3 to 4 carbon atoms, wherein the amount of said porosigen ranges from about 25 to about 70 parts by weight and has a solubility of 0.01 grams or less per 100 grams of water.

42. A process according to claim 41, wherein said copolymer is said ethylene-vinyl acetate copolymer.

43. A process according to claim 39, wherein said porosity inducing agent is selected from the group consisting of an oxide and a salt, said oxide and salt having a cation selected from the group consisting of the alkaline metals, iron, zinc, nickel, silver, and tin, and said salt having an anion selected from the group consisting of a carbonate, bicarbonate, nitrate, nitrite, nitride, peroxide, phosphate, phosphite, phosphide, sulfate, sulfite and sulfide.

44. A process according to claim 43, wherein said copolymer is said ethylene-vinyl acetate copolymer.

45. A process according to claim 43 wherein said X of said toxicant is selected from the group consisting of halogen, oxygen, and acetate, wherein said alkyl group contains from 3 to 6 carbon atoms, and wherein said aryl group is phenyl.

46. A process according to claim 45, wherein said porosity inducing agent is selected from the class consisting of iron carbonate, iron sulfate, iron sulfide, iron sulfite, nickel carbonate, nickel sulfide, zinc carbonate, zinc oxide, zinc sulfide, zinc sulfite, tin sulfide, tin oxide, silver carbonate, silver oxide, silver sulfite and lithium phosphate.

47. A process according to claim 46, wherein said copolymer is said ethylene-vinyl acetate copolymer.

48. A process according to claim 46, wherein said toxicant is selected from the group consisting of tributyltin fluoride, tributyltin oxide, triphenyltin fluoride, triphenyltin acetate, and combinations thereof.

49. A process according to claim 48, wherein the amount of ethylene by weight in said ethylene-vinyl acetate copolymer ranges from about 80 percent to about 93 percent, wherein the amount of ethylene in said ethylene-propylene copolymer ranges from about 45 to about 75 percent by weight, wherein the amount of said toxicant ranges from about 40 to about 70 parts by weight, and wherein the amount of said porosity inducing agent ranges from about 25 to about 60 parts by weight and has a solubility of 0.01 grams or less per 100 grams of water.

50. A process according to claim 49, wherein said copolymer is said ethylene-vinyl acetate copolymer.

51. A process according to claim 39, or 40, or 41 further including with said ethylene-vinyl acetate copolymer or said ethylene-propylene from about 30 percent to about 75 percent by weight of a low density polyethylene based upon the total weight of said polyethylene and said copolymer, said polyethylene having a density of from 0.90 to about 0.940 g/cc and a weight average molecular weight of from about 100,000 to about 400,000.

52. A process according to claim 51, wherein said toxicant is selected from the group consisting of tributyltin fluoride, tributyltin oxide, triphenyltin fluoride, triphenyltin acetate, and combinations thereof, wherein said ethylene-vinyl acetate copolymer has a melt flow index of from about 6 to about 12, wherein said low density polyethylene has a melt flow index of from about 5 to about 14, and wherein said ethylene-propylene copolymer has a melt flow index of from about 15 to about 45.

53. A process according to claim 43, or 45, or 49, further including with said ethylene-vinyl acetate copolymer or said ethylene-propylene copolymer from about 30 to about 75 percent by weight of a low density polyethylene based upon the total weight of said polyethylene and said ethylene-vinyl acetate copolymer or said ethylene-propylene copolymer, said polyethylene having a density of from about 0.90 to about 0.94 g/cc and a weight average molecular weight of from about 100,000 to about 400,000.

54. A process according to claim 53, wherein said ethylene-vinyl acetate has a melt flow index of from about 6 to about 12, wherein said low density polyethylene has a melt flow index of from about 5 to about 14, and wherein said ethylene-propylene copolymer has a melt flow index of from about 15 to about 45.

55. A process according to claim 54, wherein said porosity inducing agent is selected from the group consisting of iron carbonate, nickel carbonate, zinc carbonate, silver carbonate.

56. A process according to claim 55, wherein said copolymer is said ethylene-vinyl acetate copolymer.

57. A process for destroying aquatic pests by the gradual and continuous release of an organotin toxicant from a thermoplastic matrix, comprising applying said aquatic pest composition of claim 19 to an aquatic environment.

58. A process according to claim 57, wherein said porosity inducing agent is selected from the group consisting of an oxide and a salt, said salt having an anion selected from the class consisting of carbonate, bicarbonate, nitrate, nitrite, nitride, peroxide, phosphate, phosphite, phoside, sulfate, sulfite, and sulfide.

59. A process according to claim 58, wherein said X of said toxicant is selected from the group consisting of halogen, oxygen, and acetate, said alkyl group contains from 3 to 6 carbon atoms, and said aryl group is phenyl.

60. A process according to claim 59, wherein said porosity inducing agent is selected from the class consisting of magnesium carbonate, magnesium sulfide, magnesium phosphides, magnesium oxide, calcium carbonate, calcium nitride, calcium oxide, calcium phosphate, calcium phosphite, calcium sulfide, calcium sulfite, barium carbonate, barium nitride, barium peroxide, barium phosphate, barium sulfate, barium sulfite, berrylium oxide, strontium carbonate, strontium sulfate, and strontium sulfite.

61. A process according to claim 60, wherein said toxicant is selected from the group consisting of tributyltin fluoride, tributyltin oxide, triphenyltin fluoride, triphenyltin acetate, and combinations thereof.

62. A process according to claim 43, wherein the amount of ethylene in said ethylene-propylene copolymer ranges from about 45 to about 75 percent by weight, wherein the amount of said toxicant ranges from about 40 to about 70 parts by weight, and wherein the amount of said porosity inducing agent ranges from about 25 to about 60 parts by weight and has a solubility of 0.01 grams or less per 100 grams of water.

63. A process according to claims 57, 58, or 62, including from about 30 percent to about 75 percent by weight of a low density polyethylene based upon the total weight of said low density polyethylene and said ethylene-propylene copolymer, said polyethylene having a density of from about 0.90 to about 0.940 g/cc and a weight average molecular weight of from about 100,000 to about 400,000.

64. A process according to claim 45, wherein said low density polyethylene has a melt flow index of from about 5 to about 14 and wherein said ethylenepropylene copolymer has a melt flow index of from about 15 to about 45.

65. A process according to claim 64, wherein said porosity inducing agent is selected from the group consisting of magnesium carbonate, calcium carbonate, barium carbonate, and strontium carbonate.

66. A process according to claim 65, wherein said porosity inducing agent is calcium carbonate.

67. A process for destroying aquatic pests by the gradual and continuous release of an organotin toxicant from a thermoplastic matrix, comprising applying said aquatic pest composition of claim 29 to an aquatic environment 68. A process for destroying aquatic pests by the gradual and continuous release of an organotin toxicant from a thermoplastic matrix, comprising applying said aquatic pest composition of claim 31 to an aquatic environment.

69. A process for destroying aquatic pests by the gradual and continuous release of an organotin toxicant from a thermoplastic matrix, comprising applying said aquatic pest composition of claim 33 to an aquatic environment.

70. A process for destroying aquatic pests by the gradual and continuous release of an organotin toxicant from a thermoplastic matrix, comprising applying said aquatic pest composition of claim 37 to an aquatic environment.

* * * * *